United States Patent [19]

Geisler et al.

[11] Patent Number: 4,809,708
[45] Date of Patent: Mar. 7, 1989

[54] METHOD AND APPARATUS FOR REAL BAR MEASUREMENTS

[75] Inventors: C. Daniel Geisler; Chi-Kong J. Chan, both of Madison, Wis.

[73] Assignee: Nicolet Instrument Corporation, Madison, Wis.

[21] Appl. No.: 85,471

[22] Filed: Aug. 12, 1987

[51] Int. Cl.⁴ .......................................... A61B 5/12
[52] U.S. Cl. ..................................... 128/746; 128/739
[58] Field of Search ....................... 128/746, 739, 774; 381/182, 186

[56] References Cited

U.S. PATENT DOCUMENTS

| Re. 29,008 | 10/1976 | Ott | 128/774 X |
|---|---|---|---|
| 3,395,697 | 8/1968 | Mendelson | 128/746 |
| 3,757,769 | 9/1973 | Arguimbau et al. | 128/746 |
| 3,882,848 | 5/1975 | Klar et al. | 128/746 |
| 3,949,735 | 4/1976 | Klar et al. | 128/746 |
| 4,009,707 | 3/1977 | Ward | 128/746 |
| 4,029,083 | 6/1977 | Baylor | 128/746 |
| 4,079,198 | 3/1978 | Bennett | 128/746 |
| 4,237,905 | 12/1980 | Keller et al. | 128/746 |
| 4,289,143 | 9/1981 | Canavesio et al. | 128/746 |
| 4,297,884 | 11/1981 | Leveque et al. | 128/774 X |
| 4,459,996 | 7/1984 | Teele | 128/746 |

OTHER PUBLICATIONS

Abstract of paper presented May 14, 1987 at the 113th Meeting of the Acoustical Society of America, Indianapolis, Indiana, and the unpublished notes reporting the content of that presentation.

M. R. Stinson, "Spatial Variation of Phase in Ducts and the Measurement of Acoustic Energy Reflection Coefficients", Journal of the Acoustical Society of America, vol. 77, No. 2, Feb. 1985, pp. 386-393.

M. R. Stinson et al, "Estimation of Acoustical Energy Reflections at the Eardrum from Measurements of Pressure Distribution in the Human Ear Canal", Journal Acoustical Society of America, vol. 72, No. 3, Sep. 1982, pp. 766-773.

F. M. Wiener, et al, "The Pressure Distribution in the Auditory Canal in a Progressive Sound Field", The Journal of the Acoustical Society of America, vol. 18, No. 2, Oct. 1946, pp. 401-408.

F. D. McDonald, "Earmold Alteration Effects as Measured in the Human Auditory Meatus", The Journal of the Acoustical Society of America, vol. 48, No. 6, Part 2, 1970, pp. 1366-1372.

(List continued on next page.)

Primary Examiner—Edward M. Coven
Assistant Examiner—Angela D. Sykes
Attorney, Agent, or Firm—Lathrop & Clark

[57] ABSTRACT

A probe tube is inserted into the ear canal of a patient to a first position in which the probe tube tip is spaced well away from the ear drum. A broad band sound signal is provided to the patient's ear and a frequency response of sound detected at the probe tube tip is taken. The probe tube tip is then moved a known distance to a second position within the ear canal, the broad band sound stimulus signal is again applied, and the frequency response of sound detected by the probe tube tip is taken. The distance of the probe tube tip from the ear drum can be determined from the two frequency responses, particularly by subtracting the frequency response in dB at one position from the frequency response in dB at the other position, and the difference frequency response will show a distinct peak at a quarter wavelength null frequency, which allows the distance of the probe tube tip from the ear drum to be estimated based on the relationship. The frequency responses measured with the probe tube at the two positions can further be used to estimate the actual sound pressure at the ear drum and the impedance of the ear drum by using relationships derived from models of the ear canal. The probe tube may be utilized with either an unoccluded ear or with an ear occluded by an ear mold; if the ear is occluded, a hearing aid delivers the sound to the ear canal through a delivery tube passing through the ear mold. A pair of probe tubes having tips spaced a known distance from one another may be used in place of the single probe tube, allowing frequency responses to be taken from both tubes simultaneously to a sound stimulus signal.

27 Claims, 5 Drawing Sheets

OTHER PUBLICATIONS

D. W. Teele et al., "Detection of Middle Ear Effusion by Acoustic Reflectometry", The Journal of Pediatrics, vol. 104, No. 6, Jun. 1984, pp. 832–838.

S. Gilman et al, "Acoustics of Ear Canal Measurement of Eardrum SPL in Simulators", Journal of the Acoustical Society of America, vol. 80, No. 3, Sep. 1986, pp. 783–793.

K. N. Stevens et al, "Calibration of Ear Canals for Audiometry at High Frequencies", Journal of the Acoustical Society of America, vol. 81, No. 2, Feb. 1987, pp. 470–484.

W. J. Murphy et al, "Two Microphone Measurement of Acoustic Intensity in the Ear Canal as a Calibration of High-Frequency Hearing".

METHOD AND APPARATUS FOR REAL BAR MEASUREMENTS

FIELD OF THE INVENTION

This invention pertains generally to the field of audiometric tests and apparatus for conducting such tests, and particularly to the measurement of sound pressure within the ear canal.

BACKGROUND OF THE INVENTION

To determine, with the greatest possible precision, the actual hearing ability of a patient, it is desirable to be able to specify that patient's response to a known sound pressure at the ear drum. Because the sound pressure at the ear drum is the pressure that drives the middle and inner ears, this pressure must be accurately known if the hearing deficit of an individual is to be accurately specified and a hearing aid for that individual properly calibrated. However, the sound pressure measured by a probe at a point within the ear canal away from the ear drum is not generally equal to the pressure which exists at the ear drum. The higher frequency components of a sound signal will produce standing wave patterns in the ear canal which result in a variation in the sound pressure measured by a probe tube as a function of distance of penetration of the probe into the ear canal. Consequently, existing probe tube sound pressure measuring techniques do not provide a reliable basis for estimating the actual sound pressures at the ear drum or for estimating the magnitude of possible errors if the measured ear canal sound pressure is assumed equal to the ear drum sound pressure. In addition, present techniques cannot reliably assure consistent measurements of the same individual from one test to the next since the location of the tip of the probe tube within the canal is not known with precision. Thus, probe tube tests which attempt to measure the hearing response of an individual at different times are not necessarily reliable because there is no assurance that the probe tube will be placed at the same position within the individual's ear each time that the test is taken.

SUMMARY OF THE INVENTION

In accordance with the present invention, the distance of the tip of the probe tube from the ear drum may be determined, allowing the probe tube test to be taken at a consistent location within the ear canal at different times, and thereby enhancing the reliability of test data taken on separate occasions. The invention further allows the actual sound pressure at the ear drum to be estimated based on measurements of sound pressure by a probe tube or mini-microphone whose tip is maintained a significant distance away from the ear drum. The impedance of the ear drum may also be estimated based on the probe tube measurements. The measurements and calculations are carried out using the apparatus of the invention in a simple, reliable fashion with minimal exercise of subjective judgment on the part of the operator and with rapid and precise calculation of the estimates of probe tube position, ear drum pressure, and ear drum impedance.

The measurements of ear canal sound pressure are taken by first inserting a thin, hollow probe tube or similar probe carrying a microphone at its tip, into the ear canal to a point where the tip of the probe tube is at a distance which is well away from the ear drum. Preferably, the probe tube is inserted using a mounting device on the head of the individual being tested which allows the distance by which the probe tube is advanced into or retracted from the ear canal to be measured accurately. With the probe tube tip at a first position in the ear canal, a sound stimulus signal is provided to the ear canal by, for example, using a loud speaker outside the external ear which provides sound to the ear canal through the unoccluded opening of the ear canal, or by utilizing a hearing aid or similar device which provides sound to the ear canal through an ear mold where it is desired to take measurements of an occluded ear canal.

Various conventional sound excitation signals may be used, including wide band noise, frequency chirps, frequency sweep, sequences of clicks, spectra of pure tones, etc. Each of these stimuli has effective broad band frequency content over a substantial portion of the audible frequency range. A microphone at the tip or connected to the probe tube outside the ear responds to the sound picked up at the tip and provides an electrical output signal which is digitized and operated upon to provide the frequency response of the ear canal to the sound stimulus. The probe tube is then moved inwardly or outwardly a short distance, e.g., 5 millimeters (mm), the sound stimulus is reapplied and another frequency response is obtained. One of the two frequency responses, expressed in decibels (db), is subtracted from the other, expressed in db, giving a difference frequency response which will show a minimum (null) or maximum peak at a particular frequency whose standing wave within the ear canal has a quarter wavelength distance which is equal to the distance between the probe tip and a point on the ear drum which is at the effective reflecting surface of the drum. With this frequency known, the distance of the probe tip from the ear drum (effective reflecting surface) may be readily estimated as the sound velocity divided by four times the quarter wavelength frequency. With the distance of the probe tip from the ear drum now known, the operator can move the probe tip in or out to a desired spacing from the ear drum at which audiometric measurements are to be made. This allows consistent positioning of the probe tip with respect to the ear drum when tests are taken on the same individual at different times.

Once the distance of the probe tip from the ear drum is known, an estimate of the actual sound pressure at the ear drum may be calculated using various formulas, derived from models of the ear canal and drum, which express the pressure at the ear drum as a function of the distances of the probe tube tip from the ear drum and the sound pressures measured at the two positions of the tip. The impedance of the ear drum can also be estimated utilizing the same measured data.

As an alternative to measuring sound pressure with a single probe tube at two positions within the ear canal, a dual probe system, in which the tip of one probe is spaced a known distance from the tip of the other, may be utilized. The two tubes are inserted into the ear canal and measurements from both probe tubes are taken simultaneously, thereby providing the data required to estimate the distance of the probe tips from the ear drum and the sound pressure and impedance at the ear drum.

In preferred apparatus for carrying out the present invention, a headband is utilized which mounts the probe tube with respect to the ear canal such that the probe tube can be selectively advanced into and retracted from the ear canal in substantially a straight line and in measurable increments. A computer controller provides an output signal to a loud speaker which transmits the stimulus sound signal to the ear canal. If the speaker is mounted outside the ear canal, a reference microphone also mounted outside the ear canal may be utilized to obtain base line measurements of the actual ambient sound pressure in the vicinity of the external ear. The probe tube within the ear canal is connected to a microphone which picks up the sound signal from the hollow probe tube and converts it to an electrical signal which is amplified and digitized, and the digital data is provided to the computer controller which calculates the frequency response based on the digitized signal provided thereto. For example, the digitized data may be fast Fourier transformed to obtain a frequency domain representation of the response signal picked up by the probe tube microphone. If a second, external microphone is utilized, the output of that microphone will similarly be amplified, digitized, and fast Fourier transformed to provide a base line frequency response for the stimulation signal. The frequency response of the ear canal may then be corrected, if necessary, to reflect the frequency response data picked up by the second microphone if any changes occur in the sound stimulus between the measurements at the first position of the probe tube and the measurements at the second position of the tube. With the frequency response at the probe tube calculated for both positions of the probe tube, the controller may then utilize that information and the positions of the probe tube, preferably calculated as described above, to provide estimates of the actual sound pressure at the ear drum and of the ear drum impedance. The results may then be displayed to the operator, preferably including frequency response plots for the frequency response of the ear canal at the probe tip and/or at the ear drum.

Further objects, features, and advantages of the invention will be apparent from the following detailed description when taken in conjunction with the accompanying drawings.

DESCRIPTION OF THE PREFERRED EMBODIMENT

Figure 1:
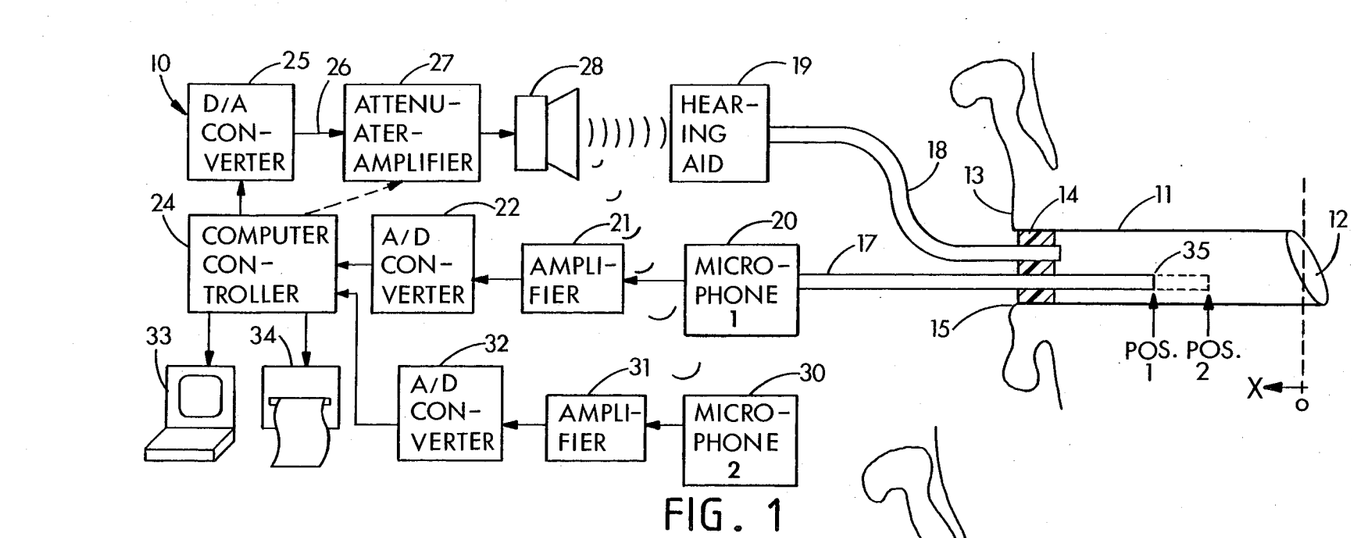
FIG. 1 is a schematic block diagram of the apparatus of the present invention shown with a schematic representation of the probe tube system placed in an ear canal.

With reference to the drawings, the apparatus of the invention for carrying out real ear measurements is shown generally at 10 in block diagram form in FIG. 1 positioned to obtain measurements on the ear canal 11 of an individual. The canal 11 terminates at one end in an ear drum shown schematically at 12, and at the other end at the external ear (concha) shown schematically at 13. For purposes of illustration, the ear canal 11 is shown occluded with an ear mold 14 at the entrance 15 (external meatus) to the canal, through which a thin hollow probe tube 17 and a sound delivery tube 18 extend into the ear canal. The delivery tube 18 is connected, in the embodiment shown, to a hearing aid 19, although the delivery tube 18 could be connected to a sound transducer which directly converts electrical stimulus signals to sound. The probe tube 17 is connected to a first microphone 20 at the end of the tube at a position outside the ear canal. The probe tube is preferably made of a soft, flexible plastic to minimize irritation of the ear canal. The microphone 20 could also be located at the inner tip of the probe tube, if the microphone is sufficiently small, with the microphone wires running through the tube to a position outside the ear canal. Where the term probe tube is used herein, it is understood to include either a hollow tube connected to a microphone outside the ear or a probe insertible in the ear having a microphone at its tip.

The apparatus 10 further includes an amplifier 21 which receives the electrical signal from the microphone, corresponding to the sound picked up by the probe tube 17, and supplies its output signal to an analog to digital converter 22. The converter 22 supplies a digitized output to a computer controller 24, which may be a conventional microcomputer system such as various IBM PC TM compatible systems. The controller 24 has the capability of providing digital output data to a digital to analog converter 25 which converts the data to an analog signal on a line 26 connected to an attenuator/amplifier 27 which provides a time varying output signal to a loud speaker 28. Thus, under the control of the computer controller 24, any desired form of sound stimulus can be provided by the loud speaker 28 to the hearing aid 19. For the best results it is preferred that the loudspeaker be positioned directly outwardly from the ear, rather than toward the front or back of the individual's head. To determine the actual sound signal that is issued by the loud speaker 28 and received by the ear, a second microphone 30 is preferably positioned near the external ear 13 so that it picks up substantially the same sound waves as the external ear or if present, the hearing aid 19. The microphone 30 provides its output signal to an amplifier 31 which supplies an analog to digital converter 32. The output of the analog to digital converter, a series of digitized signals representing the time varying signal from the microphone 30, is supplied to the computer controller 24 which uses this data in the manner described below. The computer controller is connected for input and output to a video display device and keyboard 33 and a graphic plotter 34 for permanent recordings, both of conventional design.

Tests performed in accordance with the invention can be done either with or without the hearing aid 19 and with or without occluding the entrance 15 of the ear canal by an ear mold 14. The steps taken in either case are essentially the same. First, the probe tube 17 is inserted directly through the ear opening 15 if there is no ear mold, or through a hole in the ear mold (or between the mold and the ear canal) and pushed a preselected distance into the ear canal which will place the tip 35 of the probe at a position well short of the ear drum 12 in a normal population. In adult humans, that is commonly about 12 to 15 millimeters from the ear canal entrance 15. The frequency response of the system is now taken utilizing various well-known stimuli, such as clicks, frequency chirps, broad band noise, or sequences of pure tones (preferably with random phase assigned to the tones), which are issued by the loud speaker 28 as driven by the computer controller 24. These stimuli preferably have an effective broad band of frequency components over a substantial portion of the normal audible range, e.g., over the range from 50 to 10,000 Hz. The electrical signal from the microphone 20 connected to the probe tube 17 is analyzed by the computer 24 to provide a response spectrum as a function of frequency. There will be one frequency in the frequency response of the signal picked by the microphone 20 that will have an anti-resonance dip, corresponding to the quarter wavelength null of a standing sound wave within the ear canal at the position of the probe tip. In adult humans, this frequency will most probably lie between about 5.5 kHz and 8.8 kHz when the probe tube tip is located at about the middle of the ear canal. This anti-resonance dip may be used to estimate the distance of the probe tube tip from the ear drum. However, because of additional complicated resonances occuring in the hearing aid, concha, or ear canal, it may be difficult to distinguish the quarter wavelength dip in the frequency response function. As described below, the quarter wavelength frequency, and thus the position of the probe tip, may be calculated reliably if the probe tube is moved to a second position—for example, moved inwardly to position number 2 shown in FIG. 1—and the frequency response procedure repeated. Preferably, the probe tube tip is moved a measurable distance since, as described below, the sound pressure measurements taken at the two positions of the probe tube may be utilized to calculate an estimate of sound pressure levels at the ear drum itself. The magnitude of the frequency response of the probe at the first position, in decibels (dB), is then subtracted from the frequency response (in dB) measured with the probe tip at the second position to provide a difference frequency response at each frequency data point in which most of the nulls in the probe tube frequency responses, other than the quarter wavelength null, will be eliminated, as these other nulls will generally be common to both probe tube positions. A distinct peak (and/or valley) will generally thus appear in the difference frequency response at a particular frequency, which will allow the quarter wavelength frequency to be reliably estimated. Generally, both a maximum and minimum will be observed in the response, with one of the extremes corresponding to the quarter wavelength null at one probe tube position and the other corresponding to the null at the other position. The quarter-wavelength null frequency of the point at which the probe tube was farthest from the ear drum should generally be at a lower frequency than for the point at which the probe tube was closest to the ear drum.

Of course, it is apparent that the difference frequency response can also be obtained by dividing the actual sound magnitude levels of one frequency response by the other at each frequency data point, rather than subtracting one response from the other when the responses are expressed in decibels, and the result will be entirely equivalent.

Figure 2:
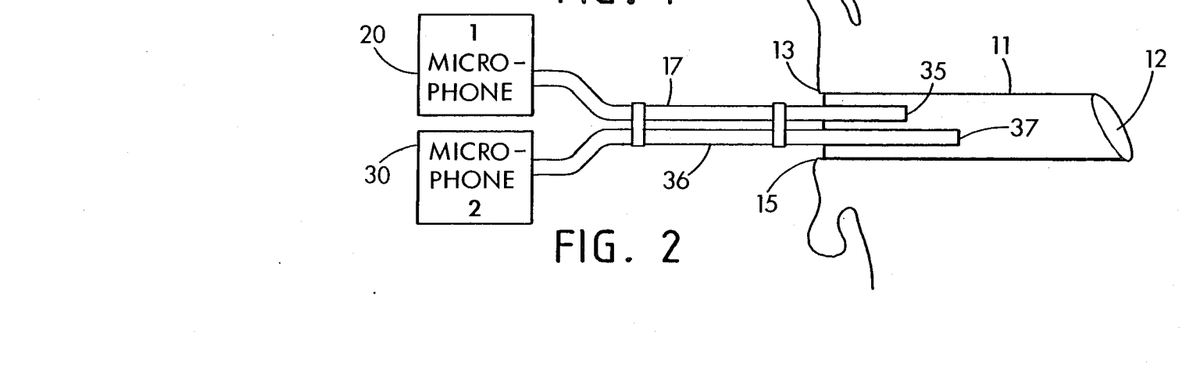
FIG. 2 is a schematic view of an alternative probe tube system using two probes.

The output of the probe tube microphone 20 at the two positions, corrected for any differences found at the second microphone 30 that might have occurred in the applied sound field between the two measurements, are used to estimate the distance of the probe tube from the ear drum at positions 1 and 2 as shown in FIG. 1, to estimate the sound pressure at the ear drum as a function of frequency, and to estimate the impedance of the ear drum as a function of frequency. The procedure set forth above can be done without the presence of the hearing aid or the ear mold. In that case, the sound from the loud speaker 28 can be provided directly to the unoccluded ear canal. The second microphone 30 may then be connected to another probe tube 36 as shown in FIG. 2, whose tip 37 is placed in the ear canal at a known distance from the tip 35 of the probe tube 17. The two measurements needed to obtain ear drum impedance or ear drum pressure can therefore be obtained simultaneously. Distances from the probe tube tips to the ear drum can also be estimated from the difference between the frequency responses of the two probe tubes. Uncorrected variations in applied sound fields between two successive repetitions of the procedure are thereby avoided. It is also apparent that if the ear mold and hearing aid are used, the probe tube (or tubes) can be inserted between the ear mold and the ear canal rather than through a port in the ear mold.

Figure 6:
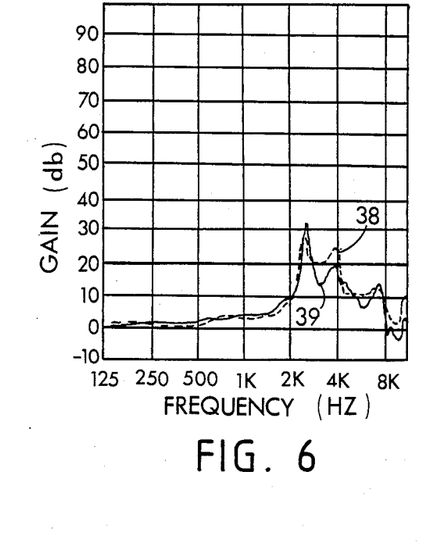
FIG. 6 is a plot of the frequency response measured with a microphone probe tube at two points in an unoccluded ear.

Exemplary frequency response plots (magnitude only, in dB) for the two positions of the probe tube in a human ear are shown in FIG. 6 as they are displayed on the display devices 33 and 34. The graph labeled 38 in FIG. 6 is the response with the probe tube at a position 15 millimeters from the ear canal entrance. The graph labeled 39 is the frequency response with the probe tube moved outwardly 5 millimeters to a position 10 millimeters in from the ear canal entrance. Both responses were taken with an unoccluded ear wherein the sound from the loud speaker 28 was provided directly to the ear canal and only the probe tube 17 was inserted into the ear canal. It is seen that the responses at the two probe tube positions are substantially similar.

Figure 7:
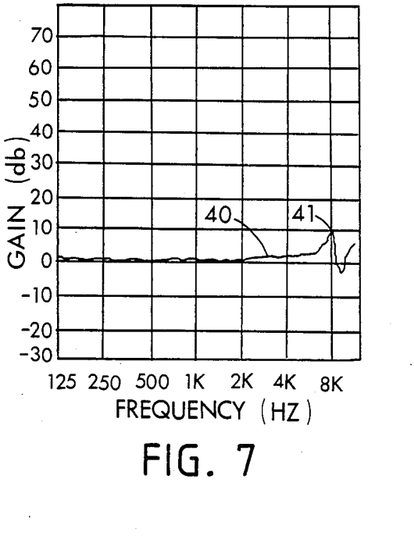
FIG. 7 is a plot of the difference frequency response for the probe tube measurements of the type shown in FIG. 6.

To obtain a difference frequency response, a frequency response of the type 39 (in dB) may then be subtracted from a frequency response of the type 38 (in dB) to provide the difference frequency response of the type illustrated by the graph 40 of FIG. 7. Equivalently, the actual magnitude of one response may be divided by the actual magnitude of the other to yield a difference frequency response function from which the quarter wavelength null frequency can be identified. The frequency responses 38 and 39 were taken using a reference microphone 30 to establish a baseline, with the responses 38 and 39 thus being relative to the magnitude of the response at the reference microphone. For purposes of determining the difference frequency response, use of the reference microphone is not necessary, and the graph 40 illustrates the difference of two frequency responses taken at the same positions as the responses 38 and 39, but without a reference microphone. The illustrative graph 40 has a (maximum) peak 41 at about 7.6 kHz, which is taken to be the quarter wavelength null point of the frequency response with the probe tube at the position number 1 (outwardmost position). The distance of the probe tube from the ear drum may then be estimated on the basis of the equation $X = c/4f$, where c is the velocity of sound and f is the frequency found from the probe transfer function, or $X = 8.65 \times 10^3/f$. For a null frequency peak of about 7.6 kHz, this yields an estimate of the position of the probe tube tip 35 at position 1 of 11.4 millimeters from the ear drum. The (negative or minimum peak) null for the graph 40 is not shown since it is off the chart in FIG. 7 at between 13 and 14 kHz.

Figure 8:
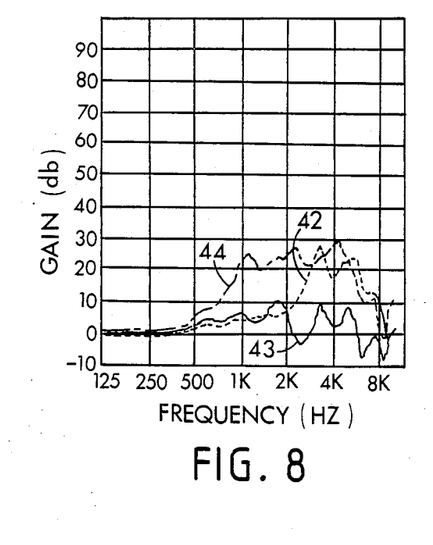
FIG. 8 are plots of frequency response of a probe tube system taken with the ear unoccluded and then with the ear occluded by an ear mold.
Figure 9:
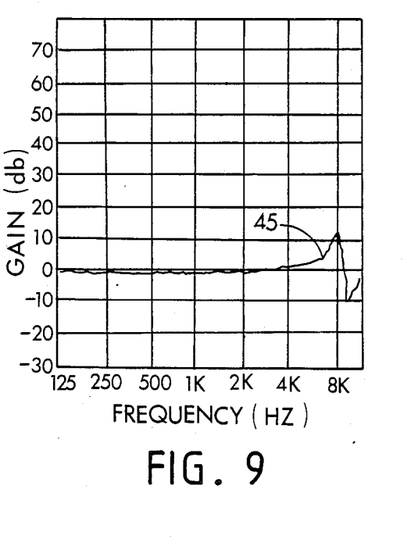
FIG. 9 is a plot of the difference frequency response for the probe tube measurements of the type shown in FIG. 8.

FIG. 8 shows the effect of the use of the ear mold 14 and hearing aid 19 on the frequency response measurements. First, a measurement was taken without an ear mold and with the probe tip inserted about 15 millimeters into the ear canal. The resulting frequency response is shown by the graph labeled 42 in FIG. 8. Another response at the same position, not referred to the reference microphone, was also taken and stored but not plotted. The probe was then moved outwardly 5 millimeters and a second frequency response was taken which was not referred to the reference microphone and is not plotted on FIG. 8. The graph labeled 45 in FIG. 9 shows the difference between the two frequency responses which were not referenced to the microphone 30 and reveals a peak at about 8 kHz, indicating that the position of the probe tip at the second position of the tube was about 10.8 millimeters from the ear drum. The probe tube was then moved to a point 15 millimeters in from the ear entrance and an ear mold with hearing aid attached was then inserted into the ear canal. A frequency response was taken at this time with the hearing aid turned off. The graph of this frequency response, shown at 43 in FIG. 8, when compared to the graph 42 shows the loss that occurs as a result of the insertion of the ear mold. The hearing aid was then turned on and another frequency response test taken, yielding the frequency response graph 44. When compared to the graph 42, the graph 44 shows the acoustic gain achieved by the hearing aid.

The frequency response data calculated by the computer controller 24 in the form of amplitude and phase values for discrete frequencies over the range of frequencies of interest may be stored by the computer controller in its memory for further processing as described below.

To estimate the sound pressure at the ear drum, it is important that the probe tip be located at a known position within the ear and that the displacements of the probe tube in and out be made in a precisely determined, measurable manner. The preferred apparatus is shown generally at 110 in FIG. 3 for purposes of illustration. It includes a headband 111 adapted to be mounted securely on the head of a patient. The headband 111 has a lateral strap 112 substantially encircling a patient's head, with a lateral adjusting mechanism 113, and a medial strap 114 attached to and extending from opposite sides of the lateral strap 112, which is itself adjusted by an adjusting mechanism 115. A protective band 116 extends across the front of the lateral strap 112 to fit against the forehead of a patient. In use, the headband 111 is slipped over the top of the head of the patient and the knobs 117 and 118 on the adjusting mechanisms 113 and 115, respectively, are turned to tighten their respective straps so that the headband is held firmly in place on the patient's head. The adjusting mechanisms 113 and 115 may be of standard construction. Two adjusting arms 119, each having an elongated main housing 120, extend outwardly from opposite sides of the lateral strap portion 112 of the headband and are mounted to the headband by a mounting means which includes a slide bar 121 and a mounting slide block 122. The slide bar 121 is secured to the lateral strap 112 by blocks 123 which are riveted or otherwise attached to the strap and to the inner side of the slide bars 121. The slide block 122 fits over the slide bar 121 and can slide back and forth thereon to allow lateral adjustment of the position of the adjusting arms 119. A thumb screw 125 on each slide block may be tightened to secure the slide block in a desired position. Each slide block 122 is preferably formed in two parts, having a first section 127 which is mounted to slide back and forth on the slide bar 121 and a second section 128, detachable from the first section, which slips into a generally V-shaped channel in the first section. The inner end of the adjusting arm housing 120 fits tightly into a socket 129 in the second section 128 and is secured in position in the socket by a thumb screw 130.

Figures 3, 4:
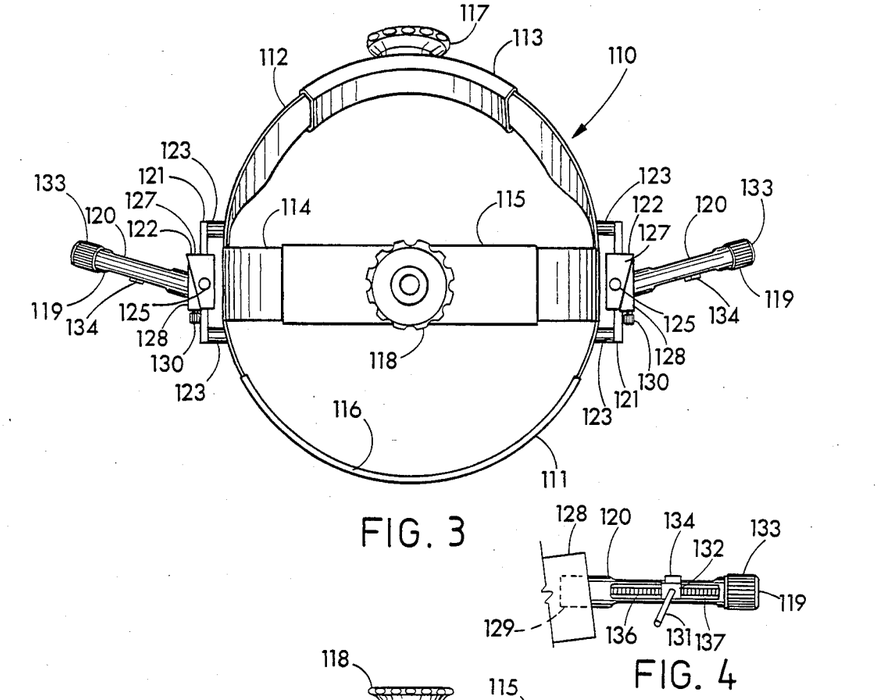
FIG. 3 is a top plan view of apparatus for positioning a microphonic probe tube which may be utilized with the present invention.
FIG. 4 is a bottom view of an adjusting arm portion of the apparatus of FIG. 3.
Figure 5:
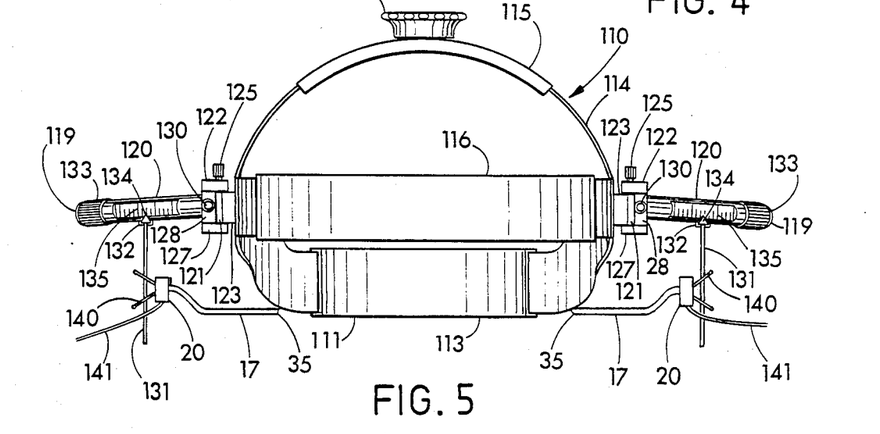
FIG. 5 is a front elevational view of the apparatus of FIG. 3.

Each adjusting arm 119 has a pendant mounting rod 131 extending downwardly therefrom which is attached to a guide 132 which slides back and forth within the arm housing 120. The position of the pendant mounting rod 131 is adjusted by turning a dial 133 at the end of the adjusting arm. The relative position of the mounting rod 131 can be determined by the operator by noting the position of an indicator 134 with respect to a scale 135 marked on the side of the arm housing 120. As best shown in FIG. 4, a bottom view of the right side of the adjusting arm 119, the guide 132 is engaged to a rotating screw 136, connected to the dial 133 by which it is rotated, such that the guide 132 will be driven back and forth by the screw 136 as the dial is rotated. The guide 132 is restrained from sideways motion by the edges of a channel 137 formed in the bottom of the arm housing 120. It is understood that the left side adjusting arm 119 and mounting means are the mirror image of but otherwise identical to the right side adjusting arm and mounting means.

The microphone 20, with the hollow plastic probe tube 17 extending from it, is mounted to the pendant rod 131 by a spring loaded clip 140 having holes therein through which the rod 131 is passed. The operator can adjust the position of the microphone 20 and the probe tube 17 vertically by grasping the two ends of the clip 140 to loosen the clip on the rod, and then moving the clip up or down until the probe tube is at the desired height. When the clip 140 is released, it holds tight in position on the rod 131. Electrical wires 141 extend from the microphone 20 to the amplifier 21.

In preparation for use of the apparatus on a patient, the operator may remove the arms 119 from the slide blocks by turning the thumb screws 130 to loosen the connection between the slide blocks and the arm housings. The knobs 117 and 118 on the adjusting mechanisms 113 and 115 are then turned to loosen the straps of the headband so that the headband will fit easily over the head of the patient. With the headband on the patient, the knobs 117 and 118 are turned to tighten the headband 111 so that it will be both comfortable to the patient but tightly held on the patient's head so that it will remain fixed with respect to the head despite any movements by the patient. If not already in place, the arms 119 are then secured into the sockets 129 in the slide blocks and secured in place with the thumb screws 130. The position of the pendant rod 131 on each adjusting arm is preferably initially set to be in a fully retracted position such that the mounting rods are as far as possible from the patient's ear. The mounting clips 140, with microphone and probe tube attached, are then slipped on the pendant rods 131. The slide blocks 122 are then moved along the slide bar 121 until the probe tube is aimed substantially down the ear canal. The height of the probe tube with respect to the ear canal may also be adjusted by moving the clips 140 up and down until the probe tube is at the height of the ear canal.

With the probe tube aimed down the ear canal, the slide blocks 122 are secured in place by tightening down the thumb screw 125. By turning the dial 133 on the end of the adjusting arm, the operator may then advance the tip 35 of the probe tube to a reference point. The ear canal entrance may be utilized as the baseline reference position, although other reference positions within the ear canal or on the external ear may also be utilized. As noted above, the probe tube will be advanced into the ear canal from the ear canal entrance an initial distance which will preferably be about half way into the ear canal but known to be safely away from the ear drum. With the probe tip at the reference point, the operator may then refer to the position of the indicator 134 with respect to the scale 135 and note the initial or reference position on the scale. The operator may then move the probe tube and probe tube tip in substantially a straight line by turning the dial 133 until the indicator 134 is moved to another position on the scale which shows a difference in position from the reference equal to the desired initial depth of the probe tube within the ear canal. At this point, the initial frequency response test may be started. The same procedure would be utilized when the ear canal is occluded by an ear mold, except that the probe tube may either be inserted between the ear mold and the wall of the ear canal or directly inserted into an opening in the ear mold with the opening of the ear mold typically being used as the initial reference point.

With measurements made in the foregoing manner yielding both the frequency response at two different positions of the probe tube within the ear canal and an estimate of the distance of the probe tube tip from the ear drum at each of the two positions, estimates can be made of the sound pressure level at the ear drum and the ear drum impedance. It is, of course, well established that the sound pressure measured in the ear canal at the probe tube tip is not the pressure at the ear drum. The following describes the preferred techniques carried out by the apparatus of the invention for obtaining the estimates of actual ear drum pressure and impedance based on models for the ear canal acoustic system.

With reference to the schematic representation of the ear canal 11 in FIG. 1, assume that the ear drum is at a point x=0. In the open ear situation shown there is an incident sound wave traveling toward the ear drum. This sound wave can be considered a plane wave, which is a reasonable assumption within the ear canal at frequencies below approximately 10 KHZ, except right at the opening 15 to the canal. Assuming that the canal can be modeled as a lossless cylindrical tube, the incident sound wave can be expressed by the equation:

$$P_I(t,x) = Re[P_I e^{jkx} e^{j\omega t}],$$

where x is the distance from the drum, $P_I$ is the maximum sound magnitude, and $k=2\pi f/c$ where c is the velocity of sound. In a similar manner a reflected wave $P_r(t, x)$ can be represented by the equation:

$$P_r(t,x) = Re[P_R e^{-jkx} e^{j\omega t}]$$

where $P_R$ is the maximum amplitude of the reflected wave.

As a consequence of the properties of sine waves, all reflected and incident waves in the ear canal at a particular frequency can be represented by the sum of these two waves. Thus, the sound pressure wave in the canal may generally be represented by the equation:

$$P(x,t) = Re[P_I e^{jkx} e^{j\omega t} + P_R e^{-jkx} e^{j\omega t}]$$

It is known that this equation can be written in the equivalent form:

$$|P(x)| = |P_I|[1+r^2+2r\cos(2kx-\theta)]^{\frac{1}{2}}$$

Where $k=2\pi f/c$, (c=velocity of sound) and $re^{j\theta} = P_r(O)/P_I(O)$, the reflection coefficient of the ear drum at the frequency f, where $\theta$ is the phase angle of the reflection coefficient.

As noted above, the first step in the measurement process is the insertion of the probe tube into the ear canal a selected distance from the ear canal entrance, say 10 millimeters. The distance at this time of the probe tube tip in the ear canal from the ear drum may be denoted as $x_1$. The sound pressure frequency response at that point $x_1$ can be denoted $P(f, x_1)$. The probe tube is then moved to the second position which is a distance $x_2$ from the ear drum and the frequency response at that point taken, which can be denoted as $P(f, x_2)$. Assuming that the impedance of the ear drum is totally resistive, the positions $x_1$ and $x_2$ of the probe tube from $x=0$ (the "effective reflecting surface" of the eardrum) may be calculated from the quarter wavelength null in the manner discussed above or may be measured in some other manner. When the probe tube is located at the first position, at the frequency of the quarter wavelength null, call it $f_1$, the last term in the equation above or $|P(x)|$ must be at a minimum, and therefore the equation at $x_1$, can be rewritten as:

$$|P(x_1)| = |P_I|(1-2r+r^2)^{\frac{1}{2}} = |P_I|(1-r)$$

Thus,
$$|P_I| = |P(x_1)|/(1-r)$$

Substituting these values in the equation for $|P(x)|$ yields:

$$|P(x)| = \frac{|P(x_1)|}{1-r}[1 + r^2 + 2r\cos(2kx - \theta)]^{\frac{1}{2}}$$

Now when the probe tube is moved a selected distance, for example, 5 millimeters, further into the ear canal to $x_2$ and the frequency response test is repeated, at the frequency $f_1$ there will be measured a sound pressure value $P(x_2, f_1)$. From the equation above, this yields:

$$|P(x_2,f_1)| = \frac{|P(x_1,f_1)|}{1-r}[1 + r^2 + 2r\cos(2kx_2 - \theta)]^{\frac{1}{2}}$$

Since in this case $x_2 = x_1 - 0.5$ (cm), this could be simplified as:

$$|P(x_2,f_1)| = \frac{|P(x_1,f_1)|}{1-r}[1 + r^2 + 2r\cos(2kx_1 - k - \theta)]^{\frac{1}{2}}$$

But since $2kx_1 - \theta = \pi$ to make the last term in the equation for $|P(x)|$ equal to a minimum value, the last term above can thus be written as $2r\cos(-k+\pi)$ or $-2r\cos k$. Thus, the equation above becomes:

$$|P(x_2,f_1)| = \frac{|P(x_1,f_1)|}{1-r}(1 + r^2 - 2r\cos k)^{\frac{1}{2}}$$

Since r is the only unkonwn in this equation, it can be solved for r. Letting $|P(x_2, f_1)| = P_2$ and $|P(x_1, f_1)| = P_1$, the equation can be rewritten as:

$$(1-r)^2 P_2^2 = P_1^2(1 + r^2 - 2r\cos k) \text{ or}$$

$$r^2(P_2^2 - P_1^2) + 2r(\cos k\, P_1^2 - P_2^2) + P_2^2 - P_1^2 = 0$$

This equation can be solved for r using the quadratic formula. The general expression for pressure as a function of distance from the drum x at the frequency $f_1$ can then be written as:

$$|P(x,f_1)| = \frac{|P(x_1,f_1)|}{1-r}\{1 + r^2 + 2r\cos[2k(x-x_1) + \pi]\}^{\frac{1}{2}}$$

The distance $x_1$ can be estimated as described above by the quarter wavelength relationship, which appears generally to be accurate within 2 millimeters. Thus, the pressure at the ear drum (x=0) at the frequency $f_1$ can be written as:

$$|P(0)| = \frac{|P(x_1,f_1)|}{1-r}[1 + r^2 + 2r\cos(-2kx_1 + \pi)]^{\frac{1}{2}}$$

It will be noted that the sound pressure can thus be determined using only quantities which are measured at positions significantly away from the ear drum.

If the impedance of the eardrum is largely resistive, and if the magnitude of the reflection coefficient r is known from other measurements (e.g. from the standing-wave ratio or from other calculations of the pressures), the eardrum pressure as a function of frequency f can be estimated directly from the two measured pressures P(x) and P(y) (without knowing the distances x and y to the eardrum). In that case the pressure at the ear drum is estimated by the equation $$|P(0,f)| = (1 - |r|)\left[\frac{P(x)P(y)^* - P(x)^*P(y)}{2j(1 - |r|^2)\sin k(x - y)}\right]^{\frac{1}{2}}$$

where * mean complex conjugate and $k = 2\pi f/c$.

In an alternative manner of calculating the pressure at the ear drum, the probe tube measurements at the two positions are taken as previously described and the positions of the probe tube tip calculated by the quarter wavelength relationship. The sound pressure level frequency response at both positions is measured and stored. Assuming a loss-less, cylindrical ear canal, and that the first position of the probe tube is x centimeters from the ear drum and the second position is y centimeters from the ear drum, the following complex equations for the sound pressure levels within the ear drum can be written using complex notation and taking as implicit the term $e^{j\omega t}$ in each term and that only the real part is of interest:

$$P(x) = P_i e^{jkx} + P_r e^{-jkx}$$

$$P(y) = P_i e^{jky} + P_r e^{-jky}$$

These two equations can be solved, since only $P_i$ and $P_r$ are unknown, to obtain:

$$P_i = \frac{P(x)e^{-jky} - P(y)e^{-jkx}}{e^{jk(x-y)} - e^{-jk(x-y)}}$$

$$P_r = \frac{P(y)e^{jkx} - P(x)e^{jky}}{e^{jk(x-y)} - e^{-jk(x-y)}}$$

Thus $P(0) = P_i + P_r =$ $$\frac{P(y)\sin kx - P(x)\sin ky}{\sin k(x-y)}$$

The amplitude at any given frequency can be found by determining the point of zero slope. Utilizing real variables, the equation above becomes:

$$|P(0,t)| =$$

$$\frac{|P(y)|\sin kx \cos(2\pi ft + \theta_1) - |P(x)|\sin ky \cos(2\pi ft + \theta_2)}{\sin k(x - y)}$$

Taking the derivative of this equation with respect to t and setting it to zero to find the peak allows the amplitude to be calculated. This may also be accomplished by writing the equations in complex form as follows:

$$|P(0,f)| = \frac{|P(y)|e^{j\theta_1}\sin kx - |P(x)|e^{j\theta_2}\sin ky}{\sin k(x - y)}$$

Letting $A = \sin kx/\sin k(x-y)$ and $B = \sin ky/\sin k(x-y)$, $$|P(0,f)| = [A^2|P(y)|^2 + B^2|P(x)|^2 - 2AB|P(x)||P(y)|\cos(\theta_1 - \theta_2)]^{\frac{1}{2}}$$

where $\theta_1$ is the frequency response phase angle at the position x and $\theta_2$ is the frequency response phase angle at the position y.

The foregoing equation can be used to estimate pressure at the ear drum at any frequency between 50 hertz and 10 kilohertz as follows: first, determine the frequency response function P(O,f) at a first point of the probe tip x=a which is unknown but well short of the drum, for example, 10 millimeters in from the canal entrance. Second, the distance "a" of this point from the ear drum is estimated from the quarter wavelength null, if detectable. The quarter wavelength null may also be determined from the difference frequency response after the frequency response at the second position is taken, as described above. Third, the probe is moved further into the ear canal a selected amount (for example, 5 millimeters) that still leaves the tip a distance b short of the drum, and the frequency response P(b, f) is taken at this point, where b is a known distance from a. Fourth, the equation above is solved, substituting x=a and y=b, for all frequencies of interest.

The measurement of $P_i$ and $P_r$ can be used in the following manner to measure ear drum impedance (to within the error limit imposed by the assumption that $\theta=0$ for the impedance characteristic).

$$Z_{eardrum} = Z(0) = \frac{P(0)}{-V(0)} = \frac{-P(0)}{\frac{1}{j2\pi f \rho}\frac{\partial P(0)}{\partial x}}$$

where $\rho$ is the density of air and V(O) is the velocity of the ear drum.

$$Z(0) = \rho c \frac{P_i + P_r}{P_i - P_r}$$

or $$Z(0) = j\rho c \frac{P(y)\sin kx - P(x)\sin ky}{P(x)\cos ky - P(y)\cos kx}$$

While the foregoing estimates of probe measurement tip position, ear drum pressure, etc., are conveniently carried out utilizing the digital computer controller 24, it is apparent that the present invention can be embodied in analog or hybrid analog-digital circuitry. It is also apparent that a small microphone insertable in the ear canal could be used in place of the probe tube to provide measurements of sound levels within the ear canal.

Figure 10:
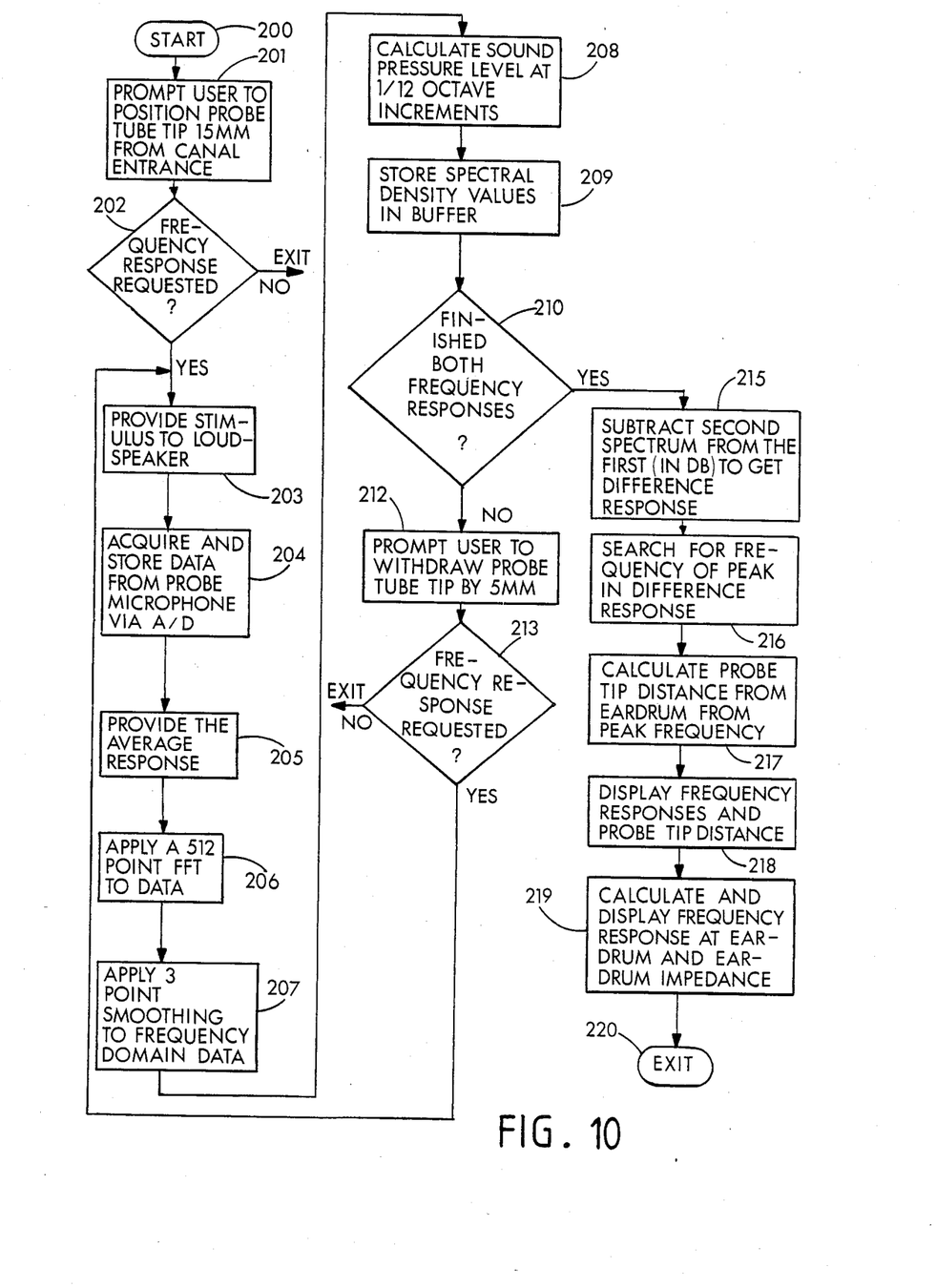
FIG. 10 is a flow diagram showing the computer program steps for determining frequency responses and the distance of the probe tube from the ear drum.

The steps carried out by the computer controller 24 under the control of its operating program when the probe position frequency responses are being determined and the probe tube tip distance from the ear drum is calculated are shown in flow diagram form in FIG. 10. Upon entry into the frequency response measurement mode (200), the controller 24 provides a display on the screen of the device 33 prompting the user to position the probe tube tip a selected distance (e.g., 15 mm) from the ear canal entrance (201). The program then waits to determine whether the user requests a frequency response (202) or an Exit and when such a request is issued, the controller provides output signal to the D/A converter 25 to provide a stimulus signal to the loud speaker (203). Simultaneously, the digital data from the A/D converter 22 coming from the probe microphone 20 is acquired, added to data of previous stimulus presentations, and stored (204). When acquisition is completed, the digitized data is divided by the number of presentations to provide the average response in the time domain (205). A Fast Fourier Transform (FFT) is then applied to the time domain data to provide corresponding frequency domain data (206) and a 3 point smoothing is then applied to the frequency domain data (207). Using this smoothed data, the program then calculates the sound pressure level in decibels (dB) at one twelfth octave increments (208) and the calculated spectral density values are stored in a buffer memory (209). The program then determines whether both frequency responses are finished (210) and if not, the computer controller provides a display on the screen 33 prompting the user to withdraw the probe tube tip by a small distance, e.g., 5 mm (212). The program then waits for the user to request a frequency response (213) or an Exit. If a response is requested, the program cycles back to block 203 to provide a stimulus to the loud speaker and thereafter proceeds through the program steps to obtain another set of frequency response spectral density values which are stored in buffer memory at a different location than the first set of spectral density values. When the program determines that both frequency responses are finished at 210, the second spectrum is subtracted from the first to get a difference response (215). The difference frequency response data is then searched to determine the frequency of the peak in the difference response (216). Using the frequency of the peak, the distance of the probe tube tip from the ear drum at one of the two positions is then calculated using the quarter wave length frequency relationship, i.e., x=c/4f where c is the velocity of sound and f is the frequency at the peak (217). Plots of the frequency responses obtained at the two positions and the calculated probe tube distance are then displayed (218) to the operator on a screen of the device 33 and, optionally, printed out using the printer 34. Optionally, the program can calculate estimates of ear drum sound pressure (219) using the sound pressures measured at the two positions of the probe tip and the foregoing calculation of the distance of the probe tip from the ear drum at the two points. Thereafter the program exits (220). If the user wishes to verify the data obtained in the first run, a command can be provided to the computer controller from the keyboard of the device 33 to restart the procedure.

Figure 11:
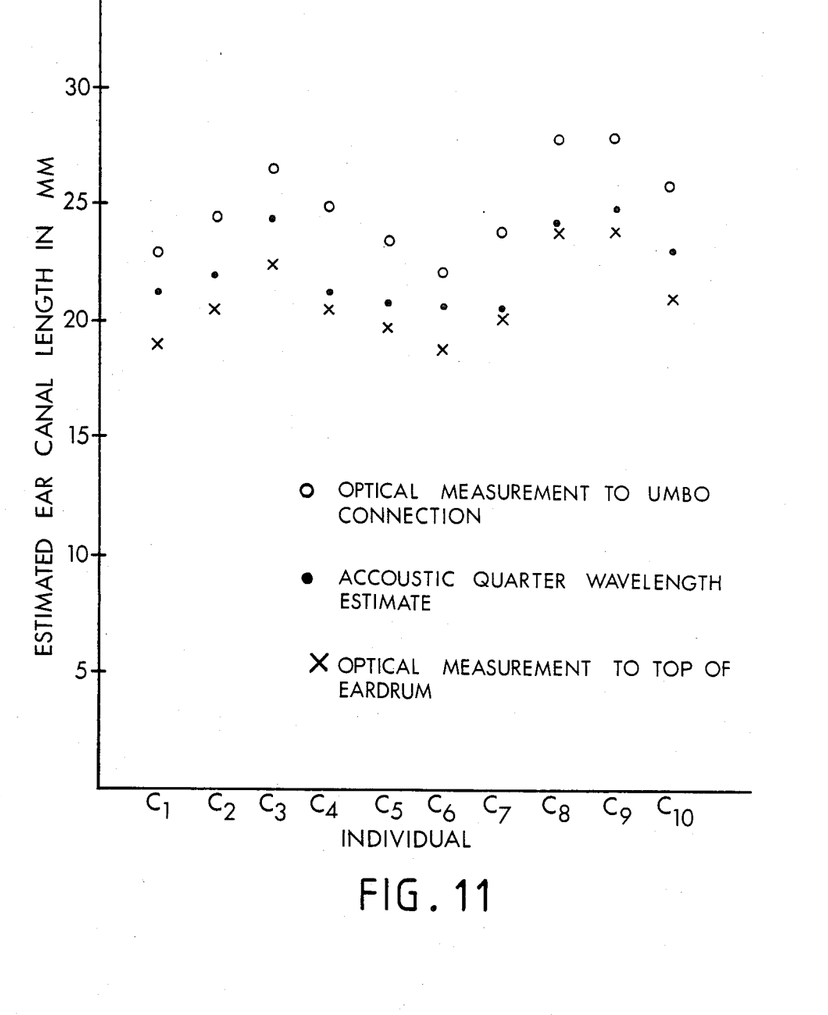
FIG. 11 is a graph illustrating the correlation between measurements of probe tube position made in accordance with the present invention and optical measurements.

As noted above, the typical human ear canal is not truly cylindrical, nor is the ear drum aligned perpendicularly to the ear canal. As illustrated somewhat schematically in FIGS. 1 and 2, the ear drum is oriented at an angle to the axis of the ear canal, and this angle can vary somewhat from individual to individual. The estimation of distance from probe tube tip to ear drum in accordance with the present invention measures the distance from the tip to an "effective reflecting plane", which is the plane within the ear at which the incoming acoustical waves would be reflected based on a model which assumes that the ear canal is truly cylindrical and the ear drum truly perpendicular to the canal. However, the distance to the drum estimated in this manner provides a good estimate of a distance from the probe tip to some point on the ear drum, a point which has been found generally to lie between the center and the top of the ear drum. The actual position of the effective reflecting plane with respect to the center of the ear drum may vary from individual to individual but will be reasonably consistent for any one individual, allowing consistent placement of the probe tube in a particular individual's ear at different times. FIG. 11 illustrates the spread of measurements made of the ear canal length (length from ear canal opening to points on the drum) of several individuals using the present invention and standard optical techniques. The optical measurements were made by focusing an operating microscope on one of two points on the ear drum and then, with the patient's head maintained stationary, moving the microscope until it can be focused on the entrance to the ear canal. The two points on the ear drum at which the microscope was focused were, the top of the ear drum and a point near the center of the ear drum where the umbo of the malleus is attached. In the chart of FIG. 11, for each of the ten individuals identified as $C_1$ through $C_{10}$, each open circle is the optically measured distance from the ear-canal entrance to the ear drum at the umbo connection, and each cross is the optically measured distance from the ear canal entrance to the top most (dorsal-most) point of the ear drum. Each solid dot is the estimate of the ear canal length using the acoustic measurements in accordance with the present invention as described above. It is seen that for all patients, the acoustic measurement in accordance with the present invention determined an "effective reflecting plane" intersecting the ear drum at a point between the top of the ear drum and the center of the ear drum.

It is understood that the invention is not confined to the particular embodiments set forth herein as illustrative, but embraces such modified forms thereof as come within the scope of the following claims.

What is claimed is:

1. A method of determining the quarter wavelength null frequency at positions within an ear canal comprising the steps of:
   (a) measuring the frequency response of the ear canal to a sound stimulus which includes frequencies in the range of interest at first and second positions in the canal which are at different distances from the ear drum;
   (b) calculating a difference frequency response based on the frequency responses measured at the two positions;
   (c) locating the frequency at which the difference frequency response has a maximum or minimum, the frequency located corresponding to the quarter wavelength null frequency at one of the positions at which the frequency response in the ear canal was measured; and
   (d) determining the distance from the effective reflecting surface of the ear drum to the point of measurement at which the quarter wavelength minimum or maximum peak occurred using the quarter wavelength frequency located from the difference frequency response.

2. The method of claim 1 wherein the step of calculating a difference frequency response is performed by subtracting the frequency response at one of the positions as measured in dB from the frequency response at the other position as measured in dB.

3. The method of claim 1 wherein the step of measuring the frequency response at the first and second positions in the ear canal is carried out using a thin hollow probe tube having a microphone at one end and an open tip at the other end, and inserting the microphone probe tube into the ear canal until the tip is at the first position, measuring the frequency response at that position, and then moving the probe tube such that the probe tube tip is at the second position and measuring the frequency response at the second position.

4. The method of claim 1 wherein the step of measuring the frequency response at the first and second positions is carried out using two separate thin hollow probe tubes having a microphone at one end of each tube and having the tips at the other ends of the tubes spaced from each other a fixed distance, and inserting the two probe tubes into the ear canal until the tips of the two tubes are at the two different positions in the ear canal at which the two frequency responses are to be measured and thereafter simultaneously measuring the frequency response of the ear canal at the tips of the two probe tubes.

5. A method of estimating the sound pressure at the ear drum in response to a sound stimulus from measurements of sound pressure at points in the ear canal spaced away from the ear drum, comprising the steps of:
   (a) measuring the frequency response of the ear canal to a sound stimulus at at least first and second positions in the ear canal located at different distances from the ear drum;
   (b) determining the distances from the ear drum of the two positions at which the frequency response measurements are made; and
   (c) determining at least the magnitude of the sound pressure frequency response at the ear drum based on the frequency responses at the two positions and the distances of the two positions from the ear drum.

6. The method of claim 5 wherein the step of measuring the frequency response at the first and second positions in the ear canal is carried out using a thin hollow probe tube having a microphone at one end and an open tip at the other end, and inserting the microphone probe tube into the ear canal until the tip is at the first position, measuring the frequency response at that position, and then moving the probe tube such that the probe tube tip is at the second position and measuring the frequency response at the second position.

7. The method of claim 5 wherein the sound stimulus has a broad band frequency content and the step of determining the distance from the ear drum includes the steps of subtracting the frequency response measured in dB at one of the positions from the frequency response measured in dB at the other position to provide a difference frequency response, locating the frequency at which the difference frequency response has a maximum or minimum peak, corresponding to the quarter wavelength null frequency, and using the quarter wavelength frequency located from the difference frequency response to determine the distance from the ear drum to the point of measurement at which the quarter wavelength minimum or maximum peak occurred.

8. The method of claim 5 wherein the step of measuring the frequency response at the first and second positions is carried out using two separate thin hollow probe tubes having a microphone at one end of each tube and a tip at the other end of each tube and having the tips of the tubes spaced from each other a fixed distance, and inserting the two probe tubes into the ear canal until the tips of the two tubes are at the first and second positions in the ear canal at which the two frequency responses are to be measured and thereafter simultaneously measuring the frequency response of the ear canal at the tips of the two probe tubes.

9. The method of claim 5 wherein the step of determining the sound pressure at the ear drum in response to the sound stimulus is performed by determining the absolute magnitude $|P(O)|$ of the sound pressure at discrete frequencies generally designated $f_1$ in accordance with the following equation:

$$|P(0)| = \frac{|P(x_1, f_1)|}{1 - r} [1 + r^2 + 2r \cos(-2kx_1 + \pi)]^{\frac{1}{2}}$$

where $P(x_1, f_1)$ is the measured sound pressure at the one point of measurement a distance $x_1$ away from the ear drum, $f_1$ is the particular frequency of interest, and r is determined from the following equation in which $P_1$ is the absolute value of the sound pressure at the position $x_1$ away from the ear drum, $P_2$ is the absolute value of the sound pressure at the second measurement position which is a distance $x_2$ away from the ear drum, and $k = 2\pi f_1 c$, where c is the velocity of sound:

$$r^2(P_2{}^2-P_1{}^2)+2r(\cos k\ P_1{}^2-P_2{}^2)+P_2{}^2-P_1{}^2=0.$$

10. The method of claim 5 wherein the step of determining the sound pressure $|P(O)|$ at the ear drum is performed at particular selected frequencies, the sound pressure $P(x)$ is measured at a point x distant from the ear drum and the sound pressure $P(y)$ measured at a second point y distant from the ear drum in accordance with the following equation:

$$P(0) = \frac{P(y)\sin kx - P(x)\sin ky}{\sin k(x-y)}$$

where $k=2\pi f/c$, f is the frequency of interest and c is the velocity of sound.

11. The method of claim 5 wherein the step of determining the sound pressure at the ear drum at a particular frequency is performed by determining the absolute magnitude $|P(O)|$ of the sound pressure at selected frequencies generally designated f in accordance with the following equation:

$$|P(O)|=[A^2|P(y)|^2+B^2|P(x)|^2-2AB|P(x)||P(y)|\cos(\theta_1-\theta_2)]^{\frac{1}{2}}$$

where $P(y)$ is the pressure at the particular frequency f at the measurement point y distant from the ear drum, $P(x)$ is the pressure at the frequency f at the measurement point x distant from the ear drum, $A=\sin kx/\sin k(x-y)$, $B=\sin ky/\sin k(x-y)$, $\theta_1$ is the frequency response phase angle at the position x, $\theta_2$ is the frequency response phase angle at the position y, and $k=2\pi f/c$ where f is the frequency of interest and c is the velocity of sound.

12. The method of claim 6 wherein the step of determining the magnitude of the sound pressure at the ear drum includes the step of determining the ear drum reflection coefficient r and determining the pressure at the ear drum at a frequency f in accordance with the following equation:

$$|P(0,f)| = (1-|r|)\left[\frac{P(x)\ P(y)^* - P(x)^*\ P(y)}{2j(1-|r|^2)\sin k(x-y)}\right]^{\frac{1}{2}}$$

where $P(x)$ is the pressure at a position x, $P(y)$ is the pressure at a position y, *means complex conjugate, and $k=2\pi f/c$, where c is the velocity of sound.

13. A method of estimating the impedance of the ear drum from measurements at two different positions in the ear canal of the sound pressure frequency response of the ear canal to a sound stimulus and of the distances of the measurement positions from the ear drum, comprising the steps of:
 (a) measuring the sound pressure frequency response to the ear canal to a sound stimulus at first and second positions in the ear canal at different distances from the ear drum;
 (b) determining the distance from the ear drum of the two positions at which frequency response measurements are made;
 (c) calculating the impedance $Z(O)$ of the ear drum at selected frequencies in accordance with the following equation:

$$Z(0) = j\rho c\ \frac{P(y)\sin kx - P(x)\sin ky}{P(x)\cos ky - P(y)\cos kx}$$

where $P(x)$ is the sound pressure at a particular frequency f at the position of measurement x distant from the ear drum, $P(y)$ is the sound pressure at the frequency f at the position of measurement y distant from the ear drum, $k=2\pi f/c$, where c is the velocity of sound and $\rho$ is the density of air.

14. The method of claim 13 wherein the step of measuring the frequency response at the first and second positions in the ear canal is carried out using a thin hollow probe tube having a microphone at one end and an open tip at the other end, and inserting the microphone probe tube into the ear canal until the tip is at the first position, measuring the frequency response at that position and then moving the probe tube such that the probe tip is at the second position and measuring the frequency response at the second position.

15. The method of claim 13 wherein the sound stimulus has a broad band frequency content, and the step of determining the distance from the ear drum of the two positions includes the steps of subtracting the frequency response measured in dB at one of the positions from the frequency response measured in dB at the other position to provide a difference frequency response, locating the frequency at which the difference frequency response has a maximum or minimum peak, corresponding to the quarter wavelength null frequency, and using the quarter wavelength frequency located from the difference frequency response to calculate the distance from the ear drum of the position of measurement at which the quarter wavelength peak or dip occurred.

16. The method of claim 13 wherein the step of measuring the frequency response at the first and second positions is carried out using two separate thin hollow probe tubes having a microphone at one end of each tube and a tip at the other end of each tube and having the tips spaced from each other a fixed distance, and inserting the two probe tubes into the ear canal until the tips of the two tubes are at the first and second positions in the ear canal at which the two frequency responses are to be measured and thereafter simultaneously measuring the frequency response of the ear canal at the tips of the two probe tubes.

17. A method of locating the position of a sound measuring tip, such as the tip of a probe tube or a microphone, within an ear canal with respect to the ear drum, comprising the steps of:
 (a) mounting the sound measuring tip in position with respect to the head of a patient to be tested such that the tip will be in a fixed position with respect to the head and ear of the patient, but allowing the tip to be moved in substantially a straight line inwardly and outwardly in the ear canal;
 (b) advancing the tip into the ear canal of the patient to a first position which is known to be a substantial distance away from the ear drum;
 (c) providing a sound stimulus to the ear canal which has broad band frequency content and measuring the frequency response of the sound signal received by the tip at the first position;
 (d) moving the tip to a second position a different distance away from the ear drum than the first position but still spaced substantially away from the ear drum;

(e) providing a sound stimulus to the ear canal which has broad band frequency content and measuring the frequency response of the sound signal received by the tip at the second position;
(f) subtracting the frequency response measured in dB at one of the positions of the tip from the frequency response measured in dB at the other position of the tip to provide a difference frequency response;
(g) locating the frequency of a magnitude minimum or maximum peak in the difference frequency response corresponding to the quarter wavelength null frequency at one of the positions of the tip; and
(h) determining the distance of the tip from the ear drum at one of the positions at which the quarter wavelength null frequency was located based on the quarter wavelength relationship.

18. The method of claim 17 wherein the distance of the tip from the ear drum at the position at which the quarter wavelength null frequency was located is determined as equal to c/4f, where c is the velocity of sound and f is the frequency of the peak in the difference frequency response corresponding to the quarter wavelength null.

19. The method of claim 17 including the additional step of moving the tip inwardly or outwardly in the ear canal as necessary to bring the probe tip from the position for which its distance from the ear drum was determined to a desired reference distance from the ear drum at which audiometric tests are to be performed.

20. Apparatus for making probe tube frequency response tests in the ear canal of a patient, comprising:
(a) a thin probe tube insertible in an ear canal and having a tip;
(b) means for mounting the probe tube in a fixed position with respect to the ear of a patient such that the probe tube tip can be moved inwardly and outwardly in the ear canal selected distances in substantially a straight line;
(c) means for providing a sound stimulus signal to the ear canal of the patient which has broad band frequency content;
(d) first microphone means connected to the probe tube for converting the sound signal received at the probe tube tip to an electrical signal; and
(e) controller means for analyzing the electrical signal from the first microphone means and generating frequency response data corresponding to the frequency content of the sound signal recieved at the probe tube tip, for analyzing two separate signals from the first microphone means which correspond to sound signals picked up by the probe tube tip at two different positions within the ear canal in response to sound stimuli and for calculating a difference frequency response based on the frequency responses measured at the two positions.

21. The apparatus of claim 20 including reference microphone means, located at a position near the external ear of the patient, for converting the sound signal which is received by it into an electrical signal and providing the electrical signal to the controller means; and
wherein the controller means includes means for analyzing the signal from the reference microphone means and providing frequency response data corresponding to the frequency content of the signal received by the reference microphone means and for providing frequency response data of the first microphone means data referenced to the reference microphone means data.

22. The apparatus of claim 20 wherein the controller means subtracts the frequency response in dB of the signal from the first microphone means at one position of the probe tube from the frequency response in dB of the signal from the first microphone means at the other position of the probe tube to provide difference frequency response data.

23. The apparatus of claim 20 including means for providing plots visible to an operator of the frequency responses at the two positions of the probe tube tip and the difference frequency response.

24. Apparatus for making probe tube frequency response tests in the ear canal of a patient, comprising:
(a) a first thin probe tube insertible in an ear canal and having a tip;
(b) a second thin probe tube insertible in an ear canal and having a tip;
(c) means for mounting the first and second probe tubes together in a fixed position with respect to the ear of the patient such that the probe tube tips can be moved inwardly and outwardly in the ear canal selected distances in substantially a straight line with the tips of the two probe tubes maintained a selected distance from one another;
(d) means for providing a sound stimulus signal to the ear canal of the patient which has braod band frequency content;
(e) first microphone means connected to the first probe tube for converting the sound signal received at the first probe tube tip to an electrical signal;
(f) second mircophone means connected to the second probe tube for converting the sound signal received at the second probe tube tip to an electrical signal; and
(g) controller means for analyzing the electrical signals from the first and second microphone means and generating frequency response data corresponding to the frequency content of the sound signals received at the first and second probe tube tips, for analyzing the signals from the first and second microphone means which correspond to sound signals picked up by the two probe tube tips at two different positions within the ear canal in response to sound stimuli, and for calculating a difference frequency response based on the frequency responses measured at the two positions.

25. The apparatus of claim 24 including reference microphone means, located at a position near the external ear of the patient, for converting the sound signal which is received by it into an electrical signal and providing the electrical signal to the controller means; and wherein the controller means includes means for analyzing the signal from the reference microphone means and providing frequency response data corresponding to the frequency content of the signal received by the reference microphone means and for providing frequency response data of the first and second microphone means data referenced to the reference microphone means data.

26. The apparatus of claim 24 including means for providing plots visible to an operator of the frequency responses at the two probe tube tips and the difference frequency response.

27. The apparatus of claim 24 wherein the controller means subtracts the frequency response in dB of the sound signal from one of the first and second microphone means from the frequency response in dB of the sound signal from the other microphone means to provide the difference frequency response data.

* * * * *

UNITED STATES PATENT AND TRADEMARK OFFICE
CERTIFICATE OF CORRECTION

PATENT NO. : 4,809,708

DATED : March 7, 1989

INVENTOR(S) : C. Daniel Geisler, Chi-Kong J. Chan

It is certified that error appears in the above-identified patent and that said Letters Patent is hereby corrected as shown below:

In the title, "Bar" should read --Ear--.

Col. 11, line 19, "unkonwn" should read --unknown--.

Signed and Sealed this

Seventh Day of November, 1989

Attest:

JEFFREY M. SAMUELS

Attesting Officer      Acting Commissioner of Patents and Trademarks